United States Patent [19]

Bocher et al.

[11] 4,064,238

[45] Dec. 20, 1977

[54] ANTIBIOTIC COMPOSITION CONTAINING AN ANTIBIOTIC AND AS A POTENTIATING AGENT PYRROLIDONE CARBOXYLIC ACID OR DERIVATIVE THEREOF

[76] Inventors: Dominique Bocher, 11, rue du Moulin Vert, Paris-°; Charles Pilet, 8, avenue du Buisson, Parc-Saint-Maur, both of France

[21] Appl. No.: 606,438

[22] Filed: Aug. 21, 1975

Related U.S. Application Data

[62] Division of Ser. No. 387,611, Aug. 13, 1973, Pat. No. 3,920,814.

[30] Foreign Application Priority Data

Aug. 18, 1972 Luxembourg ............................ 65921

[51] Int. Cl.$^2$ ...................... A61K 31/65; A61K 31/71; A61K 31/625; A61K 31/545
[52] U.S. Cl. .................................... 424/227; 424/181; 424/229; 424/246; 424/271; 424/274
[58] Field of Search ............................... 424/227, 274

[56] References Cited
PUBLICATIONS

Chemical Abstracts 63:14642f, (1965).

*Primary Examiner*—Jerome D. Goldberg
*Attorney, Agent, or Firm*—Cushman, Darby & Cushman

[57] ABSTRACT

Potentiation of the antibacterial activity of antibiotics is achieved by administering the same in combination with pyrrolidone carboxylic acid or a derivative thereof.

3 Claims, No Drawings

ANTIBIOTIC COMPOSITION CONTAINING AN ANTIBIOTIC AND AS A POTENTIATING AGENT PYRROLIDONE CARBOXYLIC ACID OR DERIVATIVE THEREOF

This is a division of application Ser. No. 387,611 filed Aug. 13, 1973 now U.S. Pat. No. 3,920,814.

The present invention relates to a pharmaceutical composition and more particularly to antibiotics and their enhanced activity in synergistic or potentiating combinations, said composition comprising an antibiotic and as a potentiating agent a member selected from the group consisting of pyrrolidone carboxylic acid and the pharmaceutically acceptable derivatives thereof, especially the salts and esters thereof.

The composition of the present invention exhibits the dual advantage of increasing the concentration of the antibiotics associated therewith in blood and tissue, and of extending the time of antibacterial activity of the antibiotic contained therein.

The pyrrolidone carboxylic acid or derivative thereof used in the composition of this invention as a potentiating agent have been reported to be useful as a medicament for its good psychonormalizing, psychotonic, mood elevating and antitoxic action.

It has now been found that when certain antibiotics are administered in combination with pyrrolidone carboxylic acid or its pharmaceutically acceptable derivatives, either severally or in admixture, there is not only achieved a remarkable potentiation of the intrinsic action of the antibiotic, said activity being shown in some cases to be more than ten times that of the antibiotic administered alone, but also an extended period of antibiotic activity.

The pharmaceutical compositions of the present invention thus constitute an undeniable advance in pharmacology, because these compositions give remarkably highly enhanced antibiotic blood levels so that it is possible to achieve significantly higher antibiotic concentrations in the blood and tissue with a given amount of antibiotic or conversely to achieve a given level with less of the antibiotic than would be the case when the antibiotic was used alone. The compositions of this invention thus also permit a significant reduction in the number of antibiotic dosages to be administered to achieve a given antibacterial activity or effect.

The present invention also provides a pharmaceutical composition comprising a pharmaceutically acceptable vehicle and mixture of at least one antibiotic selected from the group consisting of penicillin extract, semisynthetic penicillin, cephalosporin, oligosaccharide, tetracycline and sulfamethylthiadiazole, and pyrrolidone carboxylic acid or a pharmaceutically acceptable derivative thereof, especially its mineral or organic salts or its esters.

It has been observed that pyrrolidone carboxylic acid or its derivatives as defined have essentially no antibacterial action per se. Thus while the term "synergism" is used herein to describe the activity of the antibiotic and the pyrrolidone carboxylic acid or its derivative which in combination display an activity greater than the sum of the two activities when each component is used alone, the term "potentiation" is used herein synonymously with "synergism". The term "potentiation" refers to the augmenting of the activity of an antiotic agent by a substance which in itself has little or no anti-microbial activity.

This synergism or potentiation of the antibacterial action of these antibiotics by means of pyrrolidone carboxylic acid or its derivative has not yet been explained in terms of its mechanism.

The antibiotics that can be employed in combination with pyrrolidone carboxylic acid or its pharmaceutically acceptable derivatives in the compositions of the invention can be of different types. Representative penicillin extracts include penicillin G and penicillin V. Representative semisynthetic penicillins include ampicillin, hetacillin, methicillin, oxacillin, cloxacillin, dicloxacillin and carbenicillin. Representative cephalosporins include cephalothin and caphaloridin. Representative oligosaccharides include streptomycin, dihydrostreptomycin and gentamycin. Representative tetracyclines include base tetracycline, hexametaphosphate sodium tetracycline, chlortetracycline, demethylchlortetracycline, oxytetracycline, methacycline, doxycycline and minocycline or minocyn (7-dimethylamino-6-demethyl-6-deoxytetracycline). Sulfamethylthiadiazole is also known as Rufol.

These various antibiotics, of course, are well known and are, or have been, widely used as antibacterial agents.

The empirical formula of pyrrolidone carboxylic acid, $C_5H_7O_3N$ can be represented by the following formula:

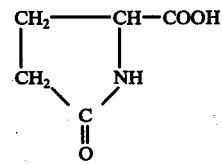

Representative pharmaceutically acceptable derivatives of pyrrolidone carboxylic acid that can be used in the present invention in combination with an antibiotic are the mineral and organic salts thereof.

Among the mineral salts that can effectively be employed are the calcium salt, the potassium salt, the sodium salt, the cobalt salt, the lithium salt, the manganese salt, the zinc salt, the copper salt, the aluminum salt, the bismuth salt, the iron salt and the magnesium salt thereof.

Among the organic salts that can effectively be used are betaine pyrrolidone carboxylate, choline pyrrolidone carboxylate, dimethylaminoethanol pyrrolidone carboxylate, methionine pyrrolidone carboxylate, lysine pyrrolidone carboxylate and diethylaminoethanol pyrrolidone carboxylate.

In accordance with the present invention, there can also be employed as the pharmaceutically acceptable derivative of pyrrolidone carboxylic acid the esters thereof and especially the alkyl esters thereof wherein the alkyl moiety has 1 to 6 carbon atoms, such as the methyl, ethyl or propyl esters, and glycerol pyrrolidone carboxylate. In accordance with a preferred embodiment of the present invention, pyrrolidone carboxylic acid alone or its lysine salt is employed.

The composition of the present invention can be administered, depending upon the particular pyrrolidone carboxylic acid or derivative thereof chosen, either orally or intravenously.

Further, the composition of the present invention can be provided in various forms depending, for instance, on the particular antibiotic selected as well as on the particular pyrrolidone carboxylic acid or derivatives thereof chosen. Thus the composition of this invention can be provided in the form of a sterile solution for intravenous administration, a powder, an effervescent or non-effervescent tablet, a gelatin capsule, an ingestible ampoule or any other form suitable for oral administration. Obviously, of course, all these forms may not be suitable for each and every antibiotic and the selection of the particular form can be dependent on the pharmacological properties of the particular antibiotic that is used. This selection, however, obviously would not encompass any undue experimentation or testing by the skilled artisan.

The effect or potentiation of the antibacterial activity of the composition of the present invention is of course a function of the quantity of pyrrolidone carboxylic acid or its derivative relative to the quantity of the selected antibiotic. In view of the diversity of the antibiotics that can be used in accordance with the present invention, it will readily be appreciated that the specific amount of pyrrolidone carboxylic acid or its derivatives can vary in rather large proportions. The amount of potentiating agent employed will be that which, in combination with the antibiotic displays greater antimicrobial activity than the corresponding antibacterial activity demonstrable from said antibiotic when used alone in equivalent amounts. Clearly this determination would involve only routine testing by those skilled in the art.

Generally, however, the weight ratio of pyrrolidone carboxylic acid or its derivatives to the selected antibiotic ranges between 1:5–100 and preferably between 1:10–50.

It has been observed in all cases that, at a certain threshold which can vary according to the particular antibiotic selected, there is a concentration of the pyrrolidone carboxylic acid or its derivatives which has no further appreciable influence on potentiation. Consequently it is not necessary to employ a concentration of this potentiating agent above these respective thresholds.

However, it must be emphasized that pyrrolidone carboxylic acid and its derivatives exhibit no toxicity whatever and can very well be used without any counterindication in amounts above the respective thresholds of the selected antibiotic.

The following examples illustrate the potentiating effect with regard to the antibacterial activity of the compositions of the present invention, using various antibiotics.

The operative technique for all the antibiotics tested was as follows:

Batches of 10 mice received, per os at time T O, a mixture of 20 mg/kg of the selected antibiotic and 1.5 g/kg of the selected pyrrolidone carboxylic acid or pharmaceutically acceptable derivative thereof.

Control batches of 10 mice received only the antibiotic in the 20 mg/kg dose.

These animals were sacrificed at 45 minutes, 2 hours, 3 hours, 5 hours and 7 hours after administration of the above described mixture or of the antibiotic alone.

The blood and hepatic level of the antibiotic was then determined from these different specimens according to the method of Grove and Randall, Assay Methods of Antibiotic, E. Med. Ency., New York 1955.

Tetracycline base
a. Quantitative determination on the serum

At the end of half an hour, the quantity of tetracycline found by quantitative determination on the serum was 10 times higher in the animals that had received the mixture of tetracycline base and pyrrolidone carboxylic acid than in animals that received tetracycline alone.

b. Quantiative determination on the liver

At the end of 5 hours, the following results were recorded:
1. control animals: tetracycline level, zero;
2. animals that had received the mixture of tetracycline + pyrrolidone carboxylic acid: tetracycline level, 1 mu;

Ampicillin
a. Quantitative determination on the serum

At the end of 7 hours, the ampicillin level in the serum of animals that had received the mixture of ampicillin and pyrrolidone carboxylic acid was eight times higher than that in the control animals that had received ampicillin alone.

b. Quantitative determination on the liver

At the end of the same time of 7 hours, the ampicillin level in the liver of the animals treated was 10 times higher than that of the control animals.

Minocycline or Minocyn
Determination on the serum

At the end of 5 hours, the determination yielded the following results:
1. control animals treated with minocycline alone: minocycline level, 0.28 mu;
2. animals treated with the mixture of minocycline and pyrrolidone carboxylic acid: minocycline level, 1 mu;

Gentamycin
a. Quantiative determination on the serum

At the end of two hours the determination yielded the following results:
1. control animals treated with gentamycin alone: gentamycin level, zero
2. animals treated with the mixture of gentamycin and pyrrolidone carboxylic acid: gentamycin level, 0.5 mu;

These results clearly demonstrate that there is on the one hand potentiation of the antibiotic effect and on the other hand an extended period of this antibacterial effect. The compositions of the present invention can thus provide considerable reduction of the actual doses of antibiotics with the same results as to efficacy as if the antibiotic were used alone.

The same phenomena as those described above have also been observed with the other previously mentioned antibiotics.

The compositions of the present invention can thus be employed for the same therapeutic purposes as those of the respective antibiotics when used alone.

The present invention also relates to the storage of the composition of this invention in two separate parts, one part containing at least one antibiotic in powder form and the other part containing pyrrolidone carboxylic acid or a pharmaceutically acceptable derivative thereof, also in powder form.

According to a variant of this two-part storage, the first part can contain pyrrolidone carboxylic acid or its derivative in solution in sterile liquid and the other part can contain the antibiotic, in powder form, the two said parts being mixed at the time of use.

Such storage is especially recommended for intravenous injections.

In accordance with yet another variant, the selected antibiotic can be stored or packaged as a solution in a sterile liquid and the other part can be stored or packaged separately and contains the pyrrolidone carboxylic acid or its derivatives as a powder.

Such storage in two parts for intravenous injections can be effected for example as ampoules, one ampoule containing the antibiotic in solution, or the pyrrolidone carboxylic acid or its derivative, and the other ampoule containing as powder the pyrrolidone carboxylic acid or its derivative, or the antibiotic.

This storage can also be effected using a bottle with two compartments separated by a wall which can be ruptured by any suitable means, so as to produce after mixing the contents of each compartment, the composition of the present invention.

The following examples illustrate the composition of the present invention.

EXAMPLES 1-3

A syrup in accordance with the present invention is prepared by admixing the following components:

| | |
|---|---|
| Ampicillin | 1.50 g |
| Pyrrolidone carboxylic acid | 15 g |
| Aromatic excipient powder for syrup in sufficient quantity to make 40 g | |

At the time of use, this mixture is suspended in sufficient water to provide 60 ml of syrup.

Example 2 is a repetition of Example 1 except that the ampicillin is replaced by penicillin G while Example 3 is a repetition of Example 1 except that ampicillin is replaced by penicillin V.

EXAMPLES 4-10

A syrup in accordance with the present invention is prepared by admixing the following components:

| | |
|---|---|
| Ampicillin | 1.50 g |
| Lysine pyrrolidone carboxylate | 20 g |
| Aromatic excipient powder for syrup in sufficient quantity to make 40 g | |

At the time of use this mixture is suspended in sufficient water to obtain 60 ml of syrup.

Examples 5-10 each are a repetition of Example 4 except that the ampicillin of Example 4 is replaced in Examples 5-10, respectively, by hetacillin, methicillin, oxacillin, cloxacillin, dicloxacillin and carbenicillin.

EXAMPLE 11

Effervescent 5 g tablets are prepared in accordance with the present invention by admixing the following components:

| | |
|---|---|
| Tetracycline | 250 mg |
| Pyrrolidone carboxylic acid | 2 g |
| Effervescent excipient in sufficient quantity to make 5 g | |

EXAMPLE 12

Effervescent tablets are prepared in accordance with the present invention by admixing the following components:

| | |
|---|---|
| Tetracycline | 250 mg |
| Lysine pyrrolidone carboxylate | 2.5 g |
| Effervescent excipient in sufficient quantity to make 4.5 g | |

EXAMPLES 13-15

A syrup in accordance with the present invention is prepared by admixing the following components:

| | |
|---|---|
| Gentamycin | 1.5 g |
| Pyrrolidone carboxylic acid | 30 g |
| Aromatic excipient for syrup in sufficient quantity to make 3.5 g | |

At the time of use this mixture is suspended in sufficient water to obtain 60 ml of syrup.

Examples 14 and 15 each are a repetition of Example 13 except that the gentamycin of Example 13 is replaced in Examples 14 and 15 by, respectively, cephalothin and cephaloridin.

EXAMPLES 16-18

A syrup in accordance with the present invention is prepared by admixing the following components:

| | |
|---|---|
| Tetracycline | 2 g |
| Lysine pyrrolidone carboxylate | 30 g |
| Aromatic excipient in sufficient quantity, for syrup, 40 g | |

At the time of use this mixture is suspended in sufficient water to obtain 60 ml of syrup.

Examples 17 and 18 each are a repetition of Example 16 except that the tetracycline of Example 16 is replaced in Examples 17 and 18 by, respectively, streptomycin and dihydrostreptomycin.

EXAMPLES 19-25

At the time of use, an aqueous solution suitable for intravenous injection is prepared by admixing the following components:

| | |
|---|---|
| Minocycline or minocyn | 3 g |
| Pyrrolidone carboxylic acid | 100 g |
| Aqueous solution for injection | 500 ml |

Examples 20-25 each are a repetition of Example 19 except that the minocycline of Example 19 is replaced in Examples 20-25 by, respectively, hexametaphosphate sodium tetracycline, chlortetracycline, demethylchlortetracycline oxytetracycline, methacyline and doxycycline.

EXAMPLE 26

An aqueous solution for intravenous injection is prepared at the time of use by admixing the following components:

| | |
|---|---|
| Ampicillin | 3.2 g |
| Lysine pyrrolidone carboxylate | 90 g |

| -continued | |
|---|---|
| Aqueous solution for injection | 500 ml |

EXAMPLE 27

A composition in accordance with the present invention is prepared by admixing the following components and packaging the resulting mixture in packets:

| Rufol | 250 mg |
|---|---|
| Pyrrolidone carboxylic acid | 5 g |

At the time of use, the contents of the packet are suspended in a sufficient amount of water to provide an aqueous composition that can be orally administered.

EXAMPLE 28

A composition prepared in accordance with the present invention is prepared, in a two part storage arrangement:

The first part contains, in powder form, 1.5 g of ampicillin in an ampoule and the second part, packaged in a bottle, contains 15 g of pyrrolidone carboxylic acid in solution in 50 ml aromatized water.

At the time of use, the contents of the ampoule are poured into the bottle, and after shaking the resulting composition is suitable for oral administration.

EXAMPLE 29

A composition is prepared according to the invention in a two part arrangement:

The first part contains, in powder form, 20 g of pyrrolidone carboxylic acid in an ampoule and, the second part also contains, in powder form, 1 g of tetracycline in an ampoule.

At the time of use the contents of the two ampoules are poured into a sufficient amount of water to provide a composition suitable for oral administration.

What is claimed is:

1. An antibiotic composition comprising a tetracycline selected from the group consisting of tetracycline base and 7-dimethylamino-6-demethyl-6- deoxytetracycline and pyrrolidone carboxylic acid, wherein the weight ratio of pyrrolidone carboxylic acid to the tetracycline ranges between 1:5–100.

2. The composition of claim 1 wherein said tetracycline is 7-dimethylamino-6-demethyl-6-deoxytetracycline.

3. The composition of claim 1 wherein said weight ratio ranges between 1:10–50.

* * * * *